US00PP31414P2

(12) United States Plant Patent
Danziger

(10) Patent No.: US PP31,414 P2
(45) Date of Patent: Jan. 28, 2020

(54) ***VERBENA* PLANT NAMED 'DVERBIPNK'**

(50) Latin Name: *Verbena hybrida*
Varietal Denomination: DVERBIPNK

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/350,543

(22) Filed: Nov. 30, 2018

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./263.1, 308
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Verbena* cultivar named 'DVERVBIPNK' is disclosed, characterized by early flowering, an abundance of pink and white bi-color flowers, semi-trailing habit and tolerance to powdery mildew. The new variety is a *Verbena*, normally produced as an outdoor garden or container plant.

2 Drawing Sheets

Figure 1:
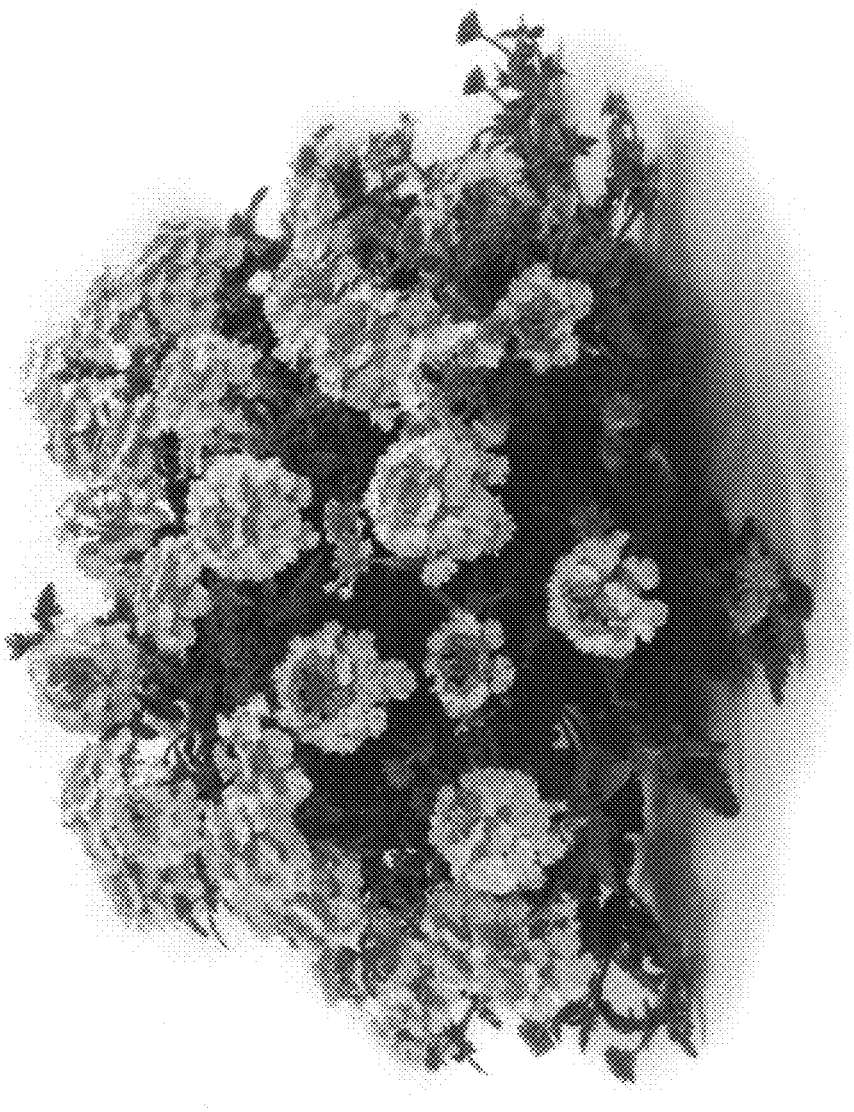

Latin name of the genus and species: *Verbena hybrida.*
Variety denomination: 'DVERVBIPNK'.

BACKGROUND OF THE INVENTION

The new *Verbena* cultivar is a product of a planned breeding program conducted by the inventor, Gavriel Danziger in Moshav Mishmar Hashiva, Israel. The objective of the breeding program was to produce new *Verbena* varieties. The cross resulting in this new variety was made during August of 2013.

The seed parent is the unpatented, propriety variety referred to as *Verbena* 'VE-12-6629'. The pollen parent is the unpatented, propriety variety referred to as *Verbena* 'VE-12-6760'. The new variety was discovered in August of 2014 by the inventor in a group of seedlings resulting from the 2013 crossing, in a greenhouse in Moshav Mishmar Hashiva, Israel. Date of first sale was Dec. 3, 2017, in Belgium. This sale was made directly by the inventor or one who obtained the claimed invention directly or indirectly from the inventor. This sale and all public disclosures made before the filing of this application fall within the exception allowed under 102(b)(1).

Asexual reproduction of the new cultivar 'DVERVBIPNK' first by vegetative cuttings was first performed during August of 2014, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DVERVBIPNK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERVBIPNK' These characteristics in combination distinguish 'DVERVBIPNK' as a new and distinct *Verbena* cultivar:

1. Flowers early.
2. Semi-trailing habit.
3. Tolerant to powdery mildew.
4. Highly floriferous plants—abundance of bi-color pink and white flowers.

PARENT COMPARISON

Plants of the new cultivar 'DVERVBIPNK' are similar to plants of the seed parent, *Verbena* 'VE-12-6629' in most horticultural characteristics, however, plants of the new cultivar 'DVERVBIPNK' differ in the following;

1. The new variety is more vigorous than parent which has weaker growing habit.
2. The flower color of the new variety is bi-color pink while the flower color of the parent is white.

Plants of the new cultivar 'DVERVBIPNK' are similar to plants of the pollen parent, *Verbena* 'VE-12-6760' in most horticultural characteristics, however, plants of the new cultivar 'DVERVBIPNK' differ in the following;

1. Candidate variety has semi-trailing habit while parent has trailing habit.

COMMERCIAL COMPARISON

Plants of the new cultivar 'DVERVBIPNK' can be compared to the commercial variety *Verbena* 'Flagdena', U.S. Plant Pat. No. 22,438. These varieties are similar in most horticultural characteristics; however, 'DVERVBIPNK' differs in the following:

1. Candidate variety is tolerant to powdery mildew whereas commercial variety is sensitive.

Plants of the new cultivar 'DVERVBIPNK' can also be compared to the commercial variety *Verbena* 'VEAZ0021', U.S. Plant Pat. No. 26,350. These varieties are similar in most horticultural characteristics; however, 'DVERVBIPNK' differs in the following:

1. Candidate variety habit is semi-trailing whereas commercial variety habit is trailing.

BRIEF DESCRIPTION OF THE PHOTOGRAPHS

The accompanying photograph in FIG. 1 illustrates in full color a typical plant of 'DVERVBIPNK' grown in in a greenhouse, in Moshav Mishmar Hashiva, Israel.

Figure 2:
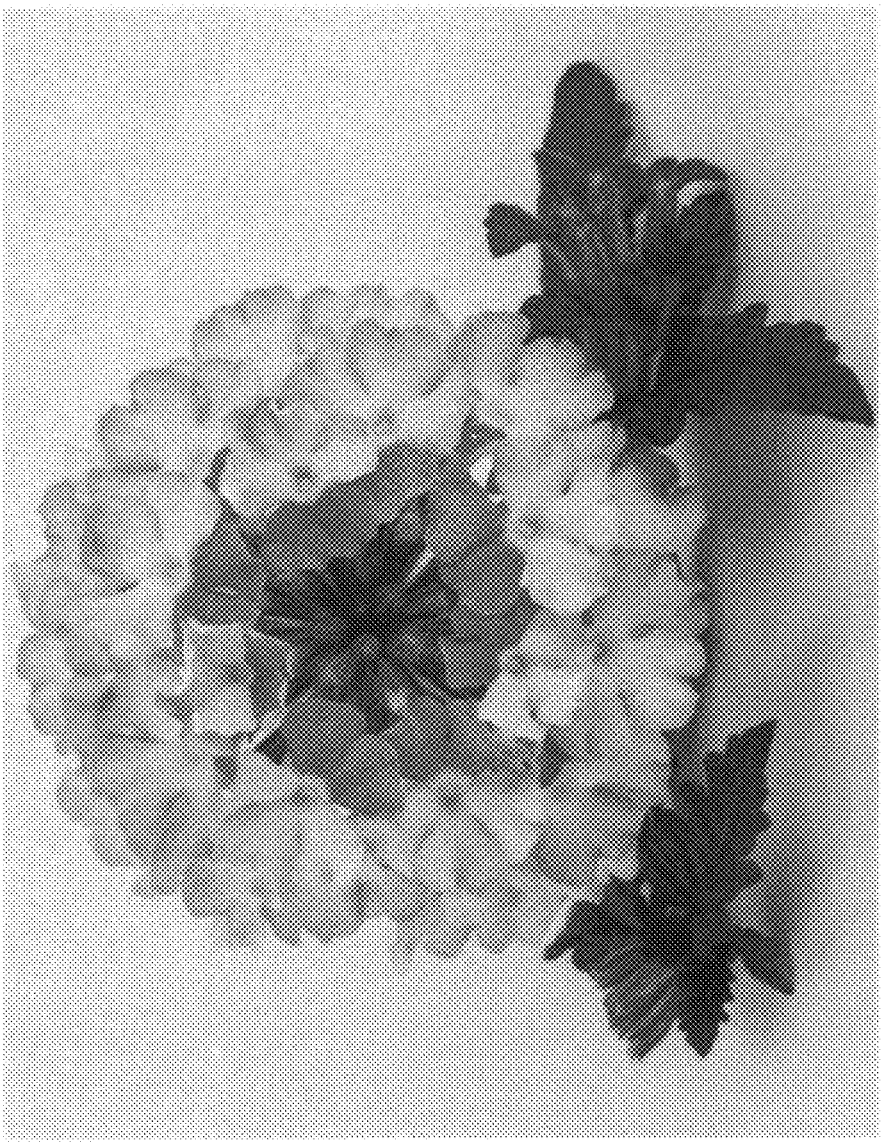

FIG. 2 illustrates in full color a typical inflorescence of 'DVERVBIPNK'. Age of the plant photographed is approximately 9 weeks from a rooted cutting in a 12 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVERVBIPNK' plants grown in a nursery in Moshav Mishmar Hashiva, Israel, under natural lighting. Measurements were taken during Autumn of 2018. The plants were approximately 80 days from a rooted cutting in a 12 cm pot. The growing temperature ranged from 18° C. to 27° C. during the days, 10° C. to 15° C. during the nights. Measurements and numerical values represent averages of typical plant types.

Botanical classification: *Verbena hybrida* 'DVERVBIPNK'.

PROPAGATION

Time to initiate roots: 7 to 9 days at optimal temperature of approximately 23° C.

Root description: Fibrous, tan to white, not accurately measured with the R.H.S. chart.

PLANT

Growth habit: Semi-trailing.
Pot size of plant described: 12 cm.
Height: 12 cm.
Plant spread: 35 cm.
Growth rate: Fast.
Branching characteristics: Freely branching.
Length of primary lateral branches: 27 cm.
Diameter of lateral branches: 0.3 cm.
Quantity of primary lateral branches: Approximately 8.
Characteristics of primary lateral branches:
- *Form*.—Cylindrical.
- *Diameter*.—0.3 cm.
- *Color*.—Near Yellow-Green 144C.
- *Texture*.—Pubescent.
- *Strength*.—Flexible.

Internode length: 3 cm.

FOLIAGE

Leaf:
- *Arrangement*.—Opposite.
- *Quantity*.—Approximately 18 per branch.
- *Average length*.—4 cm.
- *Average width*.—2 cm.
- *Shape of blade*.—Diamond-shaped.
- *Apex*.—Acute.
- *Base*.—Acute.
- *Margin*.—Serrate.
- *Texture of top surface*.—Pubescent.
- *Pubescence*.—Strigose.
- *Aspect*.—45 degrees.
- *Color*.—Young foliage upper side: Near Green 138A. Young foliage under side: Near Green 138B. Mature foliage upper side: Near Green N137B. Mature foliage under side: Near Green 138A.
- *Venation*.—Type: Pinnate. Venation color upper side: Near Yellow-Green 144C. Venation color under side: Near Yellow-Green 144D.
- *Petiole*.—Length: 0.5 cm. Diameter: 0.2 cm. Color: Near Yellow-green 144D. Texture: Pubescent.

FLOWER

Natural flowering season: Spring to Autumn under conditions found in Beit Dagan, Israel.
Days to flowering from rooted cutting: 30 to 45 days.
Inflorescence and flower type and habit: Terminal cluster.
Inflorescence size:
- *Length*.—2 cm.
- *Diameter*.—4 cm.

Number of flowers per inflorescence: Approximately 25-30.
Rate of flower opening: 4 to 6 days from bud to fully opened flower.
Flower longevity on plant: 5 to 8 days.
Persistent or self-cleaning: Self-cleaning.
Bud:
- *Shape*.—Quinquangular.
- *Length*.—0.8 cm.
- *Diameter*.—0.2 cm.
- *Color*.—Near Green 139B.

Corolla:
Flower:
- *Depth*.—2.5 cm.
- *Diameter*.—2 cm.
- *Tube*.—Tube Length: 2 cm. Tube Texture: Smooth. Tube opening diameter: 0.1 cm.
- *Petals/lobes*.—Number: 5. Length: 1.0 cm. Width: 0.5 cm. Shape: Obcordate. Aspect: Upright. Margin: Entire. Texture: Smooth.

Color:
- *When opening*.—Upper lobe: Upper surface: Red-Purple N66A. Lower surface: Red-Purple 62D. Lower lobe: Upper surface: Red-Purple 62B. Lower surface: Red-Purple 62D.
- *Fully opened*.—Upper lobe: Upper surface: Red-Purple N66A. Lower surface: Red-Purple 62D. Lower lobe: Upper surface: Red-Purple 62B. Lower surface: Red-Purple 62D.
- *Throat*.—Color: White NN155A. Texture: Smooth.
- *Tube color*.—Inside: White NN155A. Outside: White NN155A.

Calyx:
- *Form*.—Tubular.
- *Length*.—1.5 cm.
- *Diameter*.—0.2 cm.
- *Sepal shape*.—Five sepals whose margins are fused-quinquangular.

*Sepal margin*.—Entire.
*Sepal texture*.—Pubescent.
*Sepal color*.—Upper surface: Green 138A. Lower surface: Green 138A.
Pedicels: None.
Fragrance: None.

REPRODUCTIVE ORGANS

Stamens:
*Number* (*per flower*).—4.
*Filament length*.—0.2 cm.
*Anthers*.—Shape: Conical. Length: 0.1 cm. Color: Yellow-Green 154B.
Pollen:
*Color*.—Green-Yellow 1A.
*Amount*.—Few.
Pistils:
*Quantity per flower*.—1.
*Length*.—2 cm.
*Styles*.—Length: 2 cm.
*Color*.—Green-Yellow 1C.
*Stigma*.—Shape: Ovoid. Color: Yellow-Green 145A.

OTHER CHARACTERISTICS

Seeds and fruits: Not observed.
Disease/pest resistance: Tolerant of powdery mildew.
Temperature tolerance: Tolerates temperatures from approximately −1° C. to 32° C.
What is claimed is:
1. A new and distinct cultivar of *Verbena* plant named 'DVERVBIPNK' as herein illustrated and described.

* * * * *